United States Patent
Frye et al.

(12) 
(10) Patent No.: US 7,655,627 B2
(45) Date of Patent: Feb. 2, 2010

(54) MUTEINS OF FIBROBLAST GROWTH FACTOR 21

(75) Inventors: Christopher Carl Frye, Bargersville, IN (US); Lihua Huang, Carmel, IN (US); Radmila Micanovic, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 147 days.

(21) Appl. No.: 11/718,636

(22) PCT Filed: Dec. 7, 2005

(86) PCT No.: PCT/US2005/044116

§ 371 (c)(1),
(2), (4) Date: May 4, 2007

(87) PCT Pub. No.: WO2006/065582

PCT Pub. Date: Jun. 22, 2006

(65) Prior Publication Data

US 2007/0293430 A1    Dec. 20, 2007

Related U.S. Application Data

(60) Provisional application No. 60/635,882, filed on Dec. 14, 2004, now abandoned.

(51) Int. Cl.
*C07K 14/50* (2006.01)
*A61K 38/18* (2006.01)

(52) U.S. Cl. .............................. 514/12; 514/2; 530/399

(58) Field of Classification Search ........................ None
See application file for complete search history.

(56) References Cited

U.S. PATENT DOCUMENTS 6,716,626 B1    4/2004    Itoh et al.
7,491,697 B2 *  2/2009    Beals et al. ................... 514/12

FOREIGN PATENT DOCUMENTS

| WO | WO 01/18172 A2 | 3/2001 |
| WO | WO 03/011213 A | 2/2003 |
| WO | WO 2004/022723 A | 3/2004 |

OTHER PUBLICATIONS

Robinson Noah E, et al., "Deamidation of human proteins", Proceedings of the National Academy of Sciences of the United States of America, vol. 98, No. 22, Oct. 23, 2001.

Robinson Noah E., et al., "Prediction of protein deamidation rates from primary and three-dimensional structure", Proceedings of the National Academy of Sciences of the United States of America, vol. 98, No. 8, Apr. 10, 2001.

* cited by examiner

*Primary Examiner*—Christine J Saoud
(74) *Attorney, Agent, or Firm*—Lynn D. Apelgren

(57) ABSTRACT

The present invention relates to novel muteins of human fibroblast growth factor 21 with reduced deamidation compared to wild-type human FGF-21. Both protein and the respective encoding nucleic acid species are disclosed. The invention also embodies vectors and host cells for the propagation of said nucleic acid sequences and the production of said muteins. Also disclosed are methods for treating type 2 diabetes, obesity, or metabolic syndrome.

4 Claims, No Drawings

MUTEINS OF FIBROBLAST GROWTH FACTOR 21

This is the national phase application, under 35 USC 371, for PCT/US2005/044116 filed 7 Dec. 2005, which, claims the benefit, under 35 USC 119(e), of U.S. Provisional Application Ser. No. 60/635,882 filed 14 Dec. 2004, now abandoned.

BACKGROUND OF THE INVENTION

1. Field of the Invention

The present invention relates to the identification of new muteins of fibroblast growth factor 21 that have reduced deamidation when compared to wild type fibroblast growth factor 21.

2. Description of the Related Art

Fibroblast growth factors are polypeptides widely expressed in developing and adult tissues (Baird et al., *Cancer Cells,* 3:239-243, 1991) and play crucial roles in multiple physiological functions including angiogenesis, mitogenesis, pattern formation, cellular differentiation, metabolic regulation and repair of tissue injury (McKeehan et al., *Prog. Nucleic Acid Res. Mol. Biol.* 59:135-176, 1998). According to the published literature, the FGF family now consists of at least twenty-three members, FGF-1 to FGF-23 (Reuss et al., *Cell Tissue Res.* 313:139-157 (2003).

Fibroblast growth factor-21 (FGF-21) has been reported to be preferentially expressed in the liver (Nishimura et al., *Biochimica et Biophysica Acta,* 1492:203-206, 2000); WO01/36640; and WO01/18172) and described as a treatment for ischemic vascular disease, wound healing, and diseases associated with loss of pulmonary, bronchia or alveolar cell function and numerous other disorders. More recently, FGF-21 has been shown to stimulate glucose-uptake in mouse 3T3-L1 adipocytes after treatment in the presence and absence of insulin, and to decrease fed and fasting blood glucose, triglycerides, and glucagon levels in ob/ob and db/db mice and 8 week old ZDF rats in a dose-dependant manner, thus, providing the basis for the use of FGF-21 as a therapy for treating diabetes and obesity (WO03/011213).

The development of recombinant DNA technology has made possible the production of foreign products such as muteins of FGF-21 in host cells in which exogenous DNA sequences coding for those products have been introduced. The advantage of this technology is that products can be produced in high yields, in highly purified form, with low risk of contamination such as viral contamination. These recombinant techniques have been widely used for the production of recombinant proteins in prokaryotic as well as eukaryotic host cells.

However, the large-scale production of recombinant products by these techniques is still limited, due to problems of expression efficiency of these exogenous DNA sequences and to intracellular degradation of the recombinant products by the host cell in which they are made. In addition, degradation of the recombinant products during purification process can also be problematic. For example, deamidation of asparaginyl (Asn) and glutaminyl (Gln) residues to produce aspartate (Asp) and glutamate (Glu) residues causes structurally and biologically important alterations in peptide and protein structures. Although deamidation occurs spontaneously in some proteins, the problem may be exacerbated in the expression and purification of recombinant proteins. (Robinson, N. E., et al., *PNAS* 98(22):12409-12413-208, 2001; Robinson, N. E., et al., *PNAS* 98(8): 4367-4372, 2001). Moreover, deamidation instability of recombinant produced proteins may be problematic in developing a preferred solution pharmaceutical formulation due to degradation of the recombinant protein after long-term storage.

The present invention solves the problem of deamidation associated with recombinant proteins by providing FGF-21 muteins that have a reduced amount of deamidation compared to wild type FGF-21. Applicants have found that the FGF-21 muteins with reduced deamidation can be produced in industrial fermentation conditions, can be pharmaceutically formulated in a solution form, and maintain the biological activity necessary to be useful to treat subjects with disorders including, but not limited to, type 2 diabetes, obesity, and metabolic syndrome.

SUMMARY OF THE INVENTION

In a first aspect, the present invention provides muteins of human FGF-21, or a biologically active peptide thereof, comprising the substitution of any amino acid except Asn or Gln for Asn 121, wherein the numbering of the amino acids is based on SEQ ID NO:1 and wherein said mutein has reduced deamidation compared to wild-type human FGF-21.

A second aspect of the present invention provides muteins of human FGF-21, or a biologically active peptide thereof, comprising the substitution of any amino acid except Asn or Gln for Asn 121, in combination with the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO:1 and wherein said mutein has reduced deamidation when compared to wild-type human FGF-21.

A third aspect of the present invention provides muteins of human FGF-21, or a biologically active peptide thereof, comprising the substitution of any amino acid except Asn or Gln for Asn 121 in combination with the substitution of a charged and/or polar but uncharged amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152; alanine 154; glutamine 156, glycine 161, serine 163, glycine 170, or serine 172, wherein the numbering of amino acids is based on SEQ ID NO:1 and wherein said mutein has reduced deamidation when compared to wild-type human FGF-21.

A fourth aspect of the present invention provides muteins of human FGF-21, or a biologically active peptide thereof, comprising the substitution of any amino acid except Asn or Gln for Asn 121 in combination with the substitution of any amino acid except Ser or Thr for Ser 167, wherein the numbering of amino acids is based on SEQ ID NO:1 and wherein said mutein has reduced deamidation and reduced capacity of O-glycosylation when compared to wild-type human FGF-21.

A fifth aspect of the present invention provides muteins of human FGF-21, or a biologically active peptide thereof, selected from the group consisting of Leu118Cys-Ala134Cys-Asn121Ala-Ser167Ala, Leu118Cys-Ala134Cys-Asn121Val-Ser167Ala, Leu118Cys-Ala134Cys-Asn121Ser-Ser167Ala, Leu118Cys-Ala134Cys-Asn121Asp-Ser167Ala, and Leu118Cys-Ala134Cys-Asn121Glu-Ser167Ala wherein the numbering of amino acids is based on SEQ ID NO:1 and wherein said mutein has reduced deamidation and reduced capacity of O-glycosylation when expressed in yeast compared to wild-type human FGF-21.

Other embodiments are drawn to polynucleotides encoding the muteins of the first, second, third, fourth, and fifth aspects, vectors containing said polynucleotides and a host cell carrying said vector. Another embodiment is drawn to processes for producing a polypeptide, to produce cells capable of producing said polypeptide and to produce a vector containing DNA encoding said polypeptide.

Yet another embodiment is drawn to methods of treating a patient exhibiting one or more of the following condition(s): obesity, type 2 diabetes, insulin resistance, hyperinsulinemia, glucose intolerance, hyperglycemia, or metabolic syndrome comprising administering to said patient in need of such treatment a therapeutically effective amount of a human FGF-21 mutein of the first, second, third or fourth aspects.

DETAILED DESCRIPTION OF THE INVENTION

For purposes of the present invention, as disclosed and claimed herein, the following terms are as defined below.

Human FGF-21 is a 208 amino acid polypeptide containing a 27 amino acid leader sequence. Human FGF-21 has ~79% amino acid identity to mouse FGF-21 and ~80% amino acid identity to rat FGF-21. Human FGF-21 is the preferred polypeptide template for the muteins of the present invention but it is recognized that one with skill in the art could readily make muteins based on an alternative mammalian FGF-21 polypeptide sequence.

The amino acid positions of the muteins of the present invention are determined from the mature human 181 amino acid FGF-21 polypeptide as shown below (SEQ ID NO:1):

The corresponding DNA sequence coding for the mature human 181 amino acid FGF-21 polypeptide is (SEQ ID NO:2):

```
CACCCCATCCCTGACTCCAGTCCTCTCCTGCAATTCGGGGGCCAAGTCCG
GCAGCGGTACCTCTACACAGATGATGCCCAGCAGACAGAAGCCCACCTGG
AGATCAGGGAGGATGGGACGGTGGGGGGCGCTGCTGACCAGAGCCCCGAA
AGTCTCCTGCAGCTGAAAGCCTTGAAGCCGGGAGTTATTCAAATCTTGGG
AGTCAAGACATCCAGGTTCCTGTGCCAGCGGCCAGATGGGGCCCTGTATG
GATCGCTCCACTTTGACCCTGAGGCCTGCAGCTTCCGGGAGCTGCTTCTT
GAGGACGGATACAATGTTTACCAGTCCGAAGCCCACGGCCTCCCGCTGCA
CCTGCCAGGGAACAAGTCCCCACACCGGGACCCTGCACCCCGAGGACCAG
CTCGCTTCCTGCCACTACCAGGCCTGCCCCCCGCACTCCCGGAGCCACCC
GGAATCCTGGCCCCCCAGCCCCCCGATGTGGGCTCCTCGGACCCTCTGAG
CATGGTGGGACCTTCCCAGGGCCGAAGCCCCAGCTACGCTTCC
```

Amino acids are identified using the three-letter code or alternatively are designated using the standard one letter code. Mutations are designated by the three-letter code for the original amino acid, followed by the amino acid number, followed by the three-letter code for the replacement amino acid. The numerical designations of each mutein is based on the 181 amino acid sequence of mature, wild-type, human FGF-21. For example, a substitution for serine at position 167 (i.e. Ser167) with the non-polar/hydrophobic amino acid, alanine (Ala), is designated as Ser167Ala or S167A. In a similar fashion, the double substitution for leucine at position 118 and alanine at position 134 (Leu118, Ala134) with the sulfur containing amino acid, cysteine (Cys) is designated as Leu118Cys/Ala134Cys, L118C/A134C or L118C-A134C.

A "human FGF-21 mutein" is defined as comprising human FGF-21 in which at least one amino acid of the wild-type mature protein has been substituted by another amino

```
1                            10                           20
His Pro Ile Pro Asp Ser Ser Pro Leu Leu Gln Phe Gly Gly Gln Val Arg Gln Arg Tyr 30                           40
Leu Tyr Thr Asp Asp Ala Gln Gln Thr Glu Ala His Leu Glu Ile Arg Glu Asp Gly Thr 50                           60
Val Gly Gly Ala Ala Asp Gln Ser Pro Glu Ser Leu Leu Gln Leu Lys Ala Leu Lys Pro 70                           80
Gly Val Ile Gln Ile Leu Gly Val Lys Thr Ser Arg Phe Leu Cys Gln Arg Pro Asp Gly 90                           100
Ala Leu Tyr Gly Ser Leu His Phe Asp Pro Glu Ala Cys Ser Phe Arg Glu Leu Leu Leu 110                          120
Glu Asp Gly Tyr Asn Val Tyr Gln Ser Glu Ala His Gly Leu Pro Leu His Leu Pro Gly 130                          140
Asn Lys Ser Pro His Arg Asp Pro Ala Pro Arg Gly Pro Ala Arg Phe Leu Pro Leu Pro 150                          160
Gly Leu Pro Pro Ala Leu Pro Glu Pro Pro Gly Ile Leu Ala Pro Gln Pro Pro Asp Val 170                          180
Gly Ser Ser Asp Pro Leu Ser Met Val Gly Pro Ser Gln Gly Arg Ser Pro Ser Tyr Ala

Ser
``` acid. Examples of FGF-21 muteins are described in U.S. patent applications 60/528,582, 60/606,805, and 60/606,830, herein incorporated by reference. Generally speaking, a mutein possesses some modified property, structural or functional, of the wild-type protein. For example, the mutein may have enhanced or improved physical stability in concentrated solutions (e.g., less hydrophobic mediated aggregation), while maintaining a favorable bioactivity profile. The mutein may possess increased compatibility with pharmaceutical preservatives (e.g., m-cresol, phenol, benzyl alcohol), thus enabling the preparation of a preserved pharmaceutical formulation that maintains the physiochemical properties and biological activity of the protein during storage. The mutein may have reduced O-glycosylation when expressed in yeast. The mutein may have less deamidation when compared to wild-type FGF-21. The process of deamidation is a well-recognized phenomenon that may impact the stability/activity of proteins and may occur at an Asn or Gln residue. Deamidation at Asn occurs more frequently and the rate of deamidation is highly dependent on the primary, secondary and tertiary structure of the protein. Such deamidation may cause structurally or biologically important alterations in peptide or protein structure. Accordingly, muteins with reduced deamidation when compared to wild-type FGF-21, have less structural alterations, while maintaining biological potency. As used herein, these terms are not limiting, it being entirely possible that a given mutein has one or more modified properties of the wild-type protein.

A "biologically active peptide" is defined as a peptide of a mutein of the present invention that maintains the modified property(s) and the biological potency of the mutein.

The term "deamidated or deamidation" refers to the degradation of Asn or Gln residues in a protein/peptide (Robinson, et al. (2001) Proc. Natl. Acad. Sci. USA 12409-12413). For example, the intramolecular pathway for asparagine deamidation is via intermediate succinimide formation, resulting in a mixture of aspartyl and isoaspartyl residues (Harris, et al. (2001) J. of Chromatography 752:233-245). Deamidation, introducing negative change, causes structurally and biologically important alterations in peptide and protein structures and may lead to a reduction of stability and/or the reduction or loss of activity of the protein. Deamidation can occur ex vivo during the preparation of the formulated therapeutic, negatively impacting the manufacturing and storage of the pharmaceutical agent. Moreover, the deamidation can occur in vivo effecting the protein's efficacy and duration of action.

A "therapeutically-effective amount" is the minimal amount of an active agent necessary to impart therapeutic benefit to a patient. For example, a "therapeutically-effective amount" to a patient suffering or prone to suffer or to prevent it from suffering from type 2 diabetes, obesity, or metabolic syndrome is such an amount which induces, ameliorates or otherwise causes an improvement in the pathological symptoms, disease progression, physiological conditions associated with or resistance to succumbing to the afore mentioned disorders. For the purposes of the present invention a "subject" or "patient" is preferably a human.

"Type 2 diabetes" is characterized by excess glucose production in spite of the availability of insulin, and circulating glucose levels remain excessively high as a result of inadequate glucose clearance.

"Glucose intolerance" can be defined as an exceptional sensitivity to glucose.

"Hyperglycemia" is defined as an excess of sugar (glucose) in the blood.

"Hypoglycemia" also called low blood sugar, occurs when your blood glucose level drops too low to provide enough energy for your body's activities.

"Hyperinsulinemia" is defined as a higher-than-normal level of insulin in the blood.

"Insulin resistance" is defined as a state in which a normal amount of insulin produces a subnormal biologic response.

"Obesity", in terms of the human subject, can be defined as that body weight over 20 percent above the ideal body weight for a given population (R. H. Williams, Textbook of Endocrinology, 1974, p. 904-916).

"Metabolic syndrome" can be defined as a cluster of at least three of the following signs: abdominal fat—in most men, a 40-inch waist or greater; high blood sugar—at least 110 milligrams per deciliter (mg/dl) after fasting; high triglycerides—at least 150 mg/dl in the bloodstream; low HDL—less than 40 mg/dl; and, blood pressure of 130/85 or higher.

The present invention provides muteins with reduced deamidation wherein the site of deamidation is altered compared to native FGF-21. The deamidation site identified in the present invention is Asn121. Applicants have discovered that substituting any amino acid except Gln or Asn for the Asn121 site results in a significant reduction of deamidation of the expressed mutein when compared to wild-type FGF-21.

Therefore, in a first preferred aspect, the present invention provides muteins of human FGF-21, or a biologically active peptide thereof, comprising the substitution of any amino acid except Gln or Asn for Asn121, wherein the numbering of the amino acids is based on SEQ ID NO:1 and wherein said mutein has reduced deamidation when compared to wild-type human FGF-21. Preferred muteins of the first embodiment are Asn121Ala, Asn121Val, Asn121Ser, Asn121Asp, and Asn121Glu.

A second aspect of the present invention provides muteins of human FGF-21, or a biologically active peptide thereof, comprising the substitution of any amino acid except Gln or Asn for Asn121, in combination with the substitution of a cysteine for two or more of the following: arginine 19, tyrosine 20, leucine 21, tyrosine 22, threonine 23, aspartate 24, aspartate 25, alanine 26, glutamine 27, glutamine 28, alanine 31, leucine 33, isoleucine 35, leucine 37, valine 41, glycine 42, glycine 43, glutamate 50, glutamine 54, leucine 58, valine 62, leucine 66, glycine 67, lysine 69, arginine 72, phenylalanine 73, glutamine 76, arginine 77, aspartate 79, glycine 80, alanine 81, leucine 82, glycine 84, serine 85, proline 90, alanine 92, serine 94, phenylalanine 95, leucine 100, aspartate 102, tyrosine 104, tyrosine 107, serine 109, glutamate 110, proline 115, histidine 117, leucine 118, proline 119, asparagine 121, lysine 122, serine 123, proline 124, histidine 125, arginine 126, aspartate 127, alanine 129, proline 130, glycine 132, alanine 134, arginine 135, leucine 137, proline 138, or leucine 139, wherein the numbering of amino acids is based on SEQ ID NO:1 and wherein said mutein has reduced deamidation when compared to wild-type human FGF-21.

One skilled in the art will also recognize that the native cysteines, cysteine 75 and cysteine 93, could also be utilized as loci to introduce a novel disulfide bond that may impart improved properties. Specifically contemplated is the introduction of a cysteine substitution at serine 85 or phenylalanine 73, coupled with a concomitant change at either cysteine 93 or cysteine 75, respectively, wherein the latter sites are replaced with any other amino acid.

Muteins of FGF-21 with engineered disulfide bonds, in addition to the naturally occurring one at Cys75-Cys93 are described in U.S. patent application 60/528,582. The most preferred muteins of the second aspect are Leu118Cys- Ala134Cys-Asn121Asp; Leu21Cys-Leu33Cys-Asn121Asp; Ala26Cys-Lys122Cys-Asn121Asp; or Leu21Cys-Leu33Cys/Leu118Cys-Ala134Cys-Asn121Asp.

A third aspect of the present invention provides muteins of human FGF-21, or a biologically active peptide thereof, comprising the substitution of any amino acid except Gln or Asn for Asn121 in combination with the substitution of a charged and/or polar but uncharged amino acid for one or more of the amino acids at positions: glycine 42, glutamine 54, arginine 77, alanine 81, leucine 86, phenylalanine 88, lysine 122, histidine 125, arginine 126, proline 130, arginine 131, leucine 139, alanine 145, leucine 146, isoleucine 152, alanine 154, glutamine 156, glycine 161, serine 163, glycine 170, or serine 172, wherein the numbering of the amino acids is based on SEQ ID NO:1 and wherein said mutein has reduced deamidation when compared to wild-type human FGF-21.

A charged amino acid is defined as a positively- or negatively-charged amino acid. A positively charged amino acid is defined to include histidine, lysine, arginine, and non-naturally occurring analogs thereof (e.g., gamma aminobutyric acid, ornithine, etc.). A negatively charged amino acid is defined to included aspartate, glutamate, and non-naturally occurring analogs thereof (e.g., aminoadipic acid). A polar but uncharged amino acid is defined to include serine, threonine, asparagine, glutamine, and non-naturally occurring analogs thereof. Preferred muteins of the third aspect are Gln54Glu-Asn121Asp, Leu139Glu-Asn121 Asp, Ala145Glu-Asn121Asp, Leu146Glu-Asn121Asp, Ile152Glu-Asn121Asp, Gln156Glu-Asn121Asp, Ser163Glu-Asn121Asp, and Ile152Glu-Ser163Glu-Asn121Asp.

A fourth aspect of the present invention provides muteins of human FGF-21, or a biologically active peptide thereof, comprising the substitution of any amino acid except Asn or Gln for Asn121 in combination with the substitution of any amino acid except Ser or Thr for Ser167, wherein the numbering of amino acids is based on SEQ ID NO:1 and wherein said mutein has reduced deamidation and reduced capacity of O-glycosylation when expressed in yeast compared to wild-type human FGF-21. Preferred muteins of the fourth aspect are Asn121Asp-Ser167Ala, Asn121Asp-Ser167Glu, Asn121Asp-Ser167Asp, Asn121Asp-Ser167Asn, Asn121Asp-Ser167Gln, Asn121Asp-Ser167Gly, Asn121Asp-Ser167Val, Asn121Asp, Ser167His, Asn121Asp-Ser167Lys, and Asn121Asp-Ser167Tyr.

Further embodiments of the present invention provide muteins of human FGF-21, or a biologically active peptide thereof, comprising a combination of the first aspect of the present invention, the second aspect of the present invention, the third aspect of the present invention and the fourth aspect of the present invention wherein said mutein has reduced deamidation when compared to wild-type human FGF-21. Preferred muteins of this embodiment are Leu118Cys-Ala134Cys-Asn121Ala-Ser167Ala, Leu118Cys-Ala134Cys-Asn121Val-Ser167Ala, Leu118Cys-Ala134Cys-Asn121Ser-Ser167Ala, Leu118Cys-Ala134Cys-Asn121Asp-Ser167Ala, and Leu118Cys-Ala134Cys-Asn121 Glu-Ser167Ala.

Although the aspects of the present invention concern muteins of FGF-21 with reduced deamidation when compared to wild-type human FGF-21, maintaining the biological potency of the muteins as compared to wild-type FGF-21 is an important factor of consideration as well. Therefore, the biological potency of the muteins of the present invention is defined by the ability of the muteins to affect glucose uptake as measured in the in vitro 3T3-L1 cell assay (Example 2) and/or the lowering of plasma glucose levels, as well as, plasma triglycerides, as measured in vivo in the ob/ob mouse assay (Example 3).

The muteins of FGF-21 administered according to this invention may be generated and/or isolated by any means known in the art. The most preferred method for producing the mutein is through recombinant DNA methodologies and is well known to those skilled in the art. Such methods are described in *Current Protocols in Molecular Biology* (John Wiley & Sons, Inc.), which is incorporated herein by reference.

Additionally, the preferred embodiments include a biologically active peptide derived from the mutein described herein. Such a peptide will contain at least one of the substitutions described and the mutein will possess biological activity. The peptide may be produced by any means known to those skilled in the art, examples of which include but are not limited to enzymatic digestion, chemical synthesis or recombinant DNA methodologies.

It is established in the art that fragments of peptides of certain fibroblast growth factors are biologically active. See for example, Baird et al., *Proc. Natl. Acad. Sci* (USA) 85:2324-2328 (1988), and *J. Cell. Phys. Suppl.* 5:101-106 (1987). Therefore, the selection of fragments or peptides of the mutein is based on criteria known in the art. For example, it is known that dipeptidyl peptidase IV (DPP-IV) is a serine type protease involved in inactivation of neuropeptides, endocrine peptides, and cytokines (Damme et al. *Chem. Immunol.* 72: 42-56, (1999)). The N-terminus of FGF-21 (His-ProIlePro) contains two dipeptides that could potentially be substrates to DPP-IV, resulting in a fragment of FGF-21 truncated at the N-terminus by up to 4 amino acids. Unexpectedly, this fragment of wild-type FGF-21 has been demonstrated to retain biological activity (Table 1), thus, muteins of the present invention truncated at the N-terminus by up to 4 amino acids (des-HPIP) in combination with the amino acid substitutions of any of the aspects of the present invention are embodiments of the present invention. In addition, applicants have discovered that truncation of 5 amino acids or greater from the N-terminus negatively impacts biological activity. Preferred muteins of the present invention that are truncated at the N-terminus by up to 4 amino acids are des-HPIP-Leu118Cys-Ala134Cys-Asn121Asp and des-HPIP-Leu118Cys-Ala134Cys-Asn121Asp-Ser167Ala.

The present invention also encompasses polynucleotides encoding the above-described muteins that may be in the form of RNA or in the form of DNA, which DNA includes cDNA, genomic DNA, and synthetic DNA. The DNA may be double-stranded or single-stranded. The coding sequences that encode the muteins of the present invention may vary as a result of the redundancy or degeneracy of the genetic code.

The polynucleotides that encode for the muteins of the present invention may include the following: only the coding sequence for the mutein, the coding sequence for the mutein and additional coding sequence such as a functional polypeptide, or a leader or secretory sequence or a pro-protein sequence; the coding sequence for the mutein and non-coding sequence, such as introns or non-coding sequence 5' and/or 3' of the coding sequence for the mutein. Thus the term "polynucleotide encoding a mutein" encompasses a polynucleotide that may include not only coding sequence for the mutein but also a polynucleotide, which includes additional coding and/or non-coding sequence.

The present invention further relates to variants of the described polynucleotides that encode for fragments, analogs and derivatives of the polypeptide that contain the indicated substitutions. The variant of the polynucleotide may be a naturally occurring allelic variant of the human FGF-21 sequence, a non-naturally occurring variant, or a truncated variant as described above. Thus, the present invention also includes polynucleotides encoding the muteins described above, as well as variants of such polynucleotides, which variants encode for a fragment, derivative or analog of the disclosed mutein. Such nucleotide variants include deletion variants, substitution variants, truncated variants, and addition or insertion variants as long as at least one of the indicated amino acid substitutions of any of the aspects of the present invention is present.

The polynucleotides of the present invention may be expressed in mammalian, bacterial, fungal or yeast cells after the sequences have been operably linked to an expression control sequence. These expression vectors are typically replicable in the host organisms either as episomes or as an integral part of the host chromosomal DNA. Commonly, expression vectors will contain selection markers, e.g., tetracycline, neomycin, and dihydrofolate reductase, to permit detection of those cells transformed with the desired DNA sequences.

Yeast cells used for expressing the muteins of the present invention include *Pichia pastoris, Saccharomyces cerevisiae, Schizosaccharomyces pombe*, and *Pichia angust*. The yeast host cells contain suitable vectors with expression control sequences, such as promoters, including 3-phosphoglycerate kinase or other glycolytic enzymes, and an origin of replication, termination sequences and the like as desired. The preferred yeast host of the present invention is *Pichia pastoris* wherein the expression vector is integrated into the host chromosomal DNA. *Aspergillus niger, Trichoderma reesei*; and *Schizophyllum commune*, are examples of fungi hosts, although others may also be employed as a matter of choice.

The vectors containing the polynucleotide sequences of interest (e.g., the muteins of FGF-21 and expression control sequences) can be transferred into the host cell by well-known methods, which vary depending on the type of cellular host. For example, calcium chloride transfection is commonly utilized for prokaryotic cells, whereas calcium phosphate treatment or electroporation may be used for other cellular hosts.

Various methods of protein purification may be employed and such methods are known in the art and described, for example, in Deutscher, *Methods in Enzymology* 182: 83-9 (1990) and Scopes, *Protein Purification: Principles and Practice*, Springer-Verlag, NY (1982). The purification step (s) selected will depend, for example, on the nature of the production process used for the muteins of FGF-21.

The FGF-21 mutein-containing compositions should be formulated and dosed in a fashion consistent with good medical practice, taking into account the clinical condition of the patient, the site of delivery of the FGF-21 mutein composition, the method of administration, the scheduling of administration, and other factors known to practitioners. The therapeutically effective amount of the FGF-21 mutein for purposes herein is thus determined by such considerations.

The pharmaceutical compositions of the FGF-21 muteins of the present invention may be administered by any means known in the art that achieve the generally intended purpose to treat type 2 diabetes, obesity, or metabolic syndrome. The preferred route of administration is parenteral, defined herein as referring to modes of administration that include intravenous, intramuscular, intraperitoneal, intrasternal, subcutaneous, and intraarticular injection and infusion. The dosage administered will be dependent upon the age, health, and weight of the recipient, kind of concurrent treatment, if any, frequency of treatment, and the nature of the effect desired.

Compositions within the scope of the invention include all compositions wherein an FGF-21 mutein is present in an amount that is effective to achieve the desired medical effect for treatment type 2 diabetes, obesity, or metabolic syndrome. While individual needs may vary from one patient to another, the determination of the optimal ranges of effective amounts of all of the components is within the ability of the clinician of ordinary skill.

The muteins of FGF-21 of the present invention can be formulated according to known methods to prepare pharmaceutically useful compositions. A desired formulation would be one that is a stable lyophilized product that is reconstituted with an appropriate diluent or an aqueous solution of high purity with optional pharmaceutically acceptable carriers, preservatives, excipients or stabilizers [*Remington's Pharmaceutical Sciences* 16th edition (1980)]. The muteins of the present invention may be combined with a pharmaceutically acceptable buffer, and the pH adjusted to provide acceptable stability, and a pH acceptable for administration.

For parenteral administration, the FGF-21 muteins are formulated generally by mixing one or more of them at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. Preferably, one or more pharmaceutically acceptable anti-microbial agents may be added. Phenol, m-cresol, and benzyl alcohol are preferred pharmaceutically acceptable anti-microbial agents.

Optionally, one or more pharmaceutically acceptable salts may be added to adjust the ionic strength or tonicity. One or more excipients may be added to further adjust the isotonicity of the formulation. Glycerin, sodium chloride, and mannitol are examples of an isotonicity adjusting excipient.

Those skilled in the art can readily optimize pharmaceutically effective dosages and administration regimens for therapeutic compositions comprising an FGF-21 mutein, as determined by good medical practice and the clinical condition of the individual patient. The appropriate dose of an FGF-21 mutein administered will result in lowering blood glucose levels and increasing energy expenditure by faster and more efficient glucose utilization, and thus is useful for treating type 2 diabetes, obesity and metabolic syndrome. A typical dose range for the FGF-21 muteins of the present invention will range from about 0.01 mg per day to about 1000 mg per day for an adult. Preferably, the dosage ranges from about 0.1 mg per day to about 100 mg per day, more preferably from about 1.0 mg per day to about 10 mg per day. Most preferably, the dosage is about 1-5 mg per day. The appropriate dose of an FGF-21 mutein administered will result in lowering blood glucose levels and increasing energy expenditure by faster and more efficient glucose utilization, and thus is useful for treating type 2 diabetes, obesity and metabolic syndrome.

Another aspect provides muteins of FGF-21 of the present invention, or biologically active peptides thereof, for use as a medicament. Yet another aspect provides for the use of an effective amount of a mutein of human FGF-21 of the present invention, or a biologically active peptide thereof, for the manufacture of a medicament to treat a subject with obesity, type 2 diabetes, or metabolic syndrome.

Having now described the present invention in detail, the same will be more clearly understood by reference to the following examples, which are included herewith for purposes of illustration only and are not intended to be limiting of the invention.

All patents and publications referred to herein are expressly incorporated by reference.

EXAMPLE 1

Expression and Purification of FGF-21 Muteins in Yeast

FGF-21 muteins are expressed in yeast, such as *Pichia pastoris*, *Pichia methanolica* or *Saccharomyces cerevisiae*. For production in *Pichia pastoris* a commercially available system (Invitrogen, Carlsbad, Calif.) uses vectors with the powerful AOX1 (alcohol oxidase) promoters to drive high-level expression of recombinant proteins. Alternatively, vectors that use the promoter from the GAP gene (glyceraldehyde-3-phosphate dehydrogenase) are available for high level constitutive expression. The multi-copy *Pichia* expression vectors allows one to obtain strains with multiple copies of the gene of interest integrated into the genome. Increasing the number of copies of the gene of interest in a recombinant *Pichia* strain can increase protein expression levels. Yet another yeast expression system is *Saccharomyces cerevisiae*. Expression vectors contain the promoter and enhancer sequences from the GALL gene. The GAL1 promoter is one of the most widely used yeast promoters because of its strong transcriptional activity upon induction with galactose.

Analytical characterization (mass spectrum analyses) indicates that the FGF-21 muteins expressed in *Pichia pastoris* are truncated (four amino acid removal at the wild-type N-terminus). When assayed in the mouse 3T3-L1 adipocyte assay (see Example 2), this truncated variant of FGF-21 stimulates glucose uptake at the same level as wild-type FGF-21 (Table 1).

EXAMPLE 2

Glucose Uptake in Mouse 3T3-L1 Adipocytes

3T3-L1 cells are obtained from the American Type Culture Collection (ATCC, Rockville, Md.). Cells are cultured in growth medium (GM) containing 10% iron-enriched fetal bovine serum in Dulbecco's modified Eagle's medium. For standard adipocyte differentiation, two days after cells reached confluency (referred as day 0), cells are exposed to differentiation medium (DM) containing 10% fetal bovine serum, 10 µg/ml of insulin, 1 mM dexamethasone, and 0.5 µM isobutylmethylxanthine, for 48 h. Cells then are maintained in post differentiation medium containing 10% fetal bovine serum, and 10 µg/ml of insulin.

Glucose Transport Assay—Hexose uptake, as assayed by the accumulation of 0.1 mM 2-deoxy-D-[$^{14}$C]glucose, is measured as follows: 3T3-L1 adipocytes in 12-well plates are washed twice with KRP buffer (136 mM NaCl, 4.7 mM KCl, 10 mM NaPO$_4$, 0.9 mM CaCl$_2$, 0.9 mM MgSO$_4$, pH 7.4) warmed to 37° C. and containing 0.2% BSA, incubated in Leibovitz's L-15 medium containing 0.2% BSA for 2 h at 37° C. in room air, washed twice again with KRP containing, 0.2% BSA buffer, and incubated in KRP, 0.2% BSA buffer in the absence (Mg$_2$SO only) or presence of wortmannin for 30 min at 37° C. in room air. Insulin is then added to a final concentration of 100 nM for 15 min, and the uptake of 2-deoxy-D-[$^{14}$C]glucose is measured for the last 4 min. Non-specific uptake, measured in the presence of 10 µM cytochalasin B, is subtracted from all values. Protein concentrations are determined with the Pierce bicinchoninic acid assay. Uptake is measured routinely in triplicate or quadruplicate for each experiment.

The in vitro potency of muteins of FGF-21 of the present invention is compared to wild-type FGF-21 in Table 1. As indicated in Table 1, the muteins of the present invention maintained biological potency to various degrees compared to wild-type FGF-21.

TABLE 1

| FGF-21 Mutein | Expression System | EC$_{50}$ nm | Relative Potency** |
|---|---|---|---|
| des-HPIP Truncated Wild-type* | Yeast | 0.94 | 1.0 |
| des-HPIP-L118C, A134C | Yeast | 3.17 | .3 |
| des-HPIP-L118C-A134C, S167A-N121D | Yeast | 2.78 | .34 |
| des-HPIP-L118C-A134C-N121A | Yeast | 13.1 | 0.07 |
| des-HPIP-L118C-A134C-N121D | Yeast | 7.1 | 0.13 |
| des-HPIP-L118C-A134C-N121S | Yeast | 3.7 | 0.25 |

*truncated by 4 amino acids at the N-terminus
**EC$_{50}$ WT/EC$_{50}$ mutein

EXAMPLE 3

Ob/Ob Mouse Model

A study in an obesity model using male ob/ob mice is done to monitor plasma glucose levels and triglyceride levels after treatment with FGF-21, compared to vehicle and insulin control groups. The test groups of male ob/ob mice (7 weeks old) were injected with vehicle alone (0.9% NaCl), or FGF-21 mutein (0.125 mg/kg) subcutaneously (0.1 mL, once daily) for seven days. Blood is collected by tail clip bleeding on day 7, one hour after the last compound injection and plasma glucose levels were measured using a standard protocol. The ability of the FGF-21 muteins to lower plasma glucose levels and triglyceride levels as compared to the vehicle control is demonstrated with this model. The ability of the FHF-21 muteins to lower plasma glucose levels as compared to the vehicle control is shown in Table 2.

TABLE 2

| FGF-21 Mutein | Plasma Glucose levels as % of Control |
|---|---|
| Wild-type FGF-21 | 60% |
| des-HPIP-L118C-A134C-N121D | 85% |
| des-HPIP-L118C-A134C-S167A-N121D | 80% |
| des-HPIP-L118C-A134C-N121A | 78% |
| des-HPIP-L118C-A134C-S167A-N121A | 90% |

EXAMPLE 4

Deamidation of FGF-21 Muteins

Solution stability studies of the FGF-21 mutein Leu118Cys-Ala134Cys-Ser167Ala are conducted under various solvent conditions with various pH and temperature ranges. A degradation of greater than 7.5% upon storage at 25° C. for 4 weeks in PBS in the pH 6-8 range is observed. The extent of deamidation is determined by reverse phase chromatography indicating at least seven discrete peaks. The degradation products are analyzed by LC/MS/MS and the major degradation product is identified as the deamidated molecule, Asn121. After 18 months storage in solution at 5° C., approximately 19.4% degradation is observed.

As deamidation occurs, Asn121 is converted to either Asp121 or IsoAsp121. IsoAsp121 is an unnatural amino acid, and hence, may have a less favorable PK than Asn121. Thus, any naturally occurring amino acid other than Asn or Gln may be substituted for Asn121 and result in a mutein that has less deamidation than wild-type FGF-21, although it is recognized that deamidation of Gln occurs at a reduced rate compared to deamidation at Asn. Substitution for Asn121 leads not only to improving the chemical instability of an FGF-21 during the purification process but also provides a pharmaceutical solution formulation that is stable during long-term storage, an important aspect for a multi-use pharmaceutical solution formulation of an FGF-21 mutein of the present invention.

We claim:

1. A biologically active peptide of a mutein of human FGF-21 consisting of human FGF-21 containing an engineered disulfide bond wherein:
   a) cysteine is substituted for leucine 118 and alanine 134;
   b) Ala or Asp is substituted for Asn 121;
   c) Ala is substituted for Ser 167, wherein the numbering of amino acids is based on SEQ ID NO:1; and
   d) one, two, three, or four amino acids are truncated from the N-terminus.

2. The biologically active peptide of claim 1 selected from the group consisting of Δ(His1Pro2Ile3Pro4)-Leu118Cys-Ala134Cys-Asn121Ala-Ser167Ala and Δ(His1Pro2Ile3Pro4)-Leu118Cys-Ala134Cys-Asn121Asp-Ser167Ala, wherein the numbering of amino acids is based on SEQ ID NO:1.

3. A pharmaceutical composition comprising a therapeutically effective amount of the mutein of claim 2 and a pharmaceutically acceptable carrier.

4. A method for treating obesity, type 2 diabetes, or metabolic syndrome comprising administering to patient in need thereof, a therapeutically effective amount of the human FGF-21 mutein of claim 2.

* * * * *

SEQUENCE LISTING

```
<160> NUMBER OF SEQ ID NOS: 2

<210> SEQ ID NO 1
<211> LENGTH: 181
<212> TYPE: PRT
<213> ORGANISM: homo sapiens

<400> SEQUENCE: 1

His Pro Ile Pro Asp Ser Ser Pro Leu Leu Gln Phe Gly Gly Gln Val
1               5                   10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
65                  70                  75                  80

Ala Leu Tyr Gly Ser Leu His Phe Asp Pro Glu Ala Cys Ser Phe Arg
                85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 2
<211> LENGTH: 543
<212> TYPE: DNA
<213> ORGANISM: homo sapiens

<400> SEQUENCE: 2 cacccatcc   ctgactccag   tcctctcctg   caattcgggg   gccaagtccg   gcagcggtac      60
ctctacacag  atgatgccca   gcagacagaa   gcccacctgg   agatcaggga   ggatgggacg     120 gtgggggcg   ctgctgacca   gagccccgaa   agtctcctgc   agctgaaagc   cttgaagccg     180
ggagttattc  aaatcttggg   agtcaagaca   tccaggttcc   tgtgccagcg   gccagatggg     240
gccctgtatg  gatcgctcca   cttttgaccct  gaggcctgca   gcttccggga   gctgcttctt     300
gaggacggat  acaatgttta   ccagtccgaa   gcccacggcc   tcccgctgca   cctgccaggg     360
aacaagtccc  cacaccggga   ccctgcaccc   cgaggaccag   ctcgcttcct   gccactacca     420
```

```
ggcctgcccc ccgcactccc ggagccaccc ggaatcctgg cccccagcc ccccgatgtg      480 ggctcctcgg accctctgag catggtggga ccttcccagg gccgaagccc cagctacgct      540
tcc                                                                    543
```